(12) United States Patent
Brault-Guyon et al.

(10) Patent No.: US 10,080,881 B2
(45) Date of Patent: Sep. 25, 2018

(54) ASSEMBLY FOR MEDICAL USE FOR ADMINISTERING A PRODUCT TO A PATIENT

(71) Applicant: GUERBET, Villepinte (FR)

(72) Inventors: Nathanaëlle Brault-Guyon, Saint Secondin (FR); Morgane Hannigsberg, Saint Jean de Maurienne (FR); Philippe Guerder, Villiers le Bel (FR)

(73) Assignee: GUERBET, Villepinte (FR)

( * ) Notice: Subject to any disclaimer, the term of this patent is extended or adjusted under 35 U.S.C. 154(b) by 502 days.

(21) Appl. No.: 14/649,820

(22) PCT Filed: Dec. 5, 2013

(86) PCT No.: PCT/EP2013/075615
§ 371 (c)(1),
(2) Date: Jun. 4, 2015

(87) PCT Pub. No.: WO2014/086904
PCT Pub. Date: Jun. 12, 2014

(65) Prior Publication Data
US 2015/0306372 A1 Oct. 29, 2015

(30) Foreign Application Priority Data
Dec. 5, 2012 (FR) .................................... 12 61699

(51) Int. Cl.
*A61M 39/22* (2006.01)
*A61M 39/10* (2006.01)

(52) U.S. Cl.
CPC .......... *A61M 39/221* (2013.01); *A61M 39/10* (2013.01); *A61M 39/1011* (2013.01); *A61M 39/22* (2013.01)

(58) Field of Classification Search
CPC .. A61M 39/10; A61M 39/1011; A61M 39/22; A61M 39/221
See application file for complete search history.

(56) References Cited

U.S. PATENT DOCUMENTS 2,880,722 A * 4/1959 Dickinson, Jr. ........ A61M 5/347
285/148.13
5,176,415 A * 1/1993 Choksi .................. A61M 39/10
128/202.27
(Continued)

FOREIGN PATENT DOCUMENTS

DE 2907832 A1 9/1980
EP 0028198 A1 5/1981
(Continued)

OTHER PUBLICATIONS

French Preliminary Search Report and Written Opinion for French Application No. 1261699, dated May 16, 2013.
(Continued)

*Primary Examiner* — Nathan R Price
*Assistant Examiner* — Anh Bui
(74) *Attorney, Agent, or Firm* — Birch, Stewart, Kolasch & Birch, LLP

(57) ABSTRACT

The present invention relates to an assembly for medical use for administering a product to a patient, the assembly comprising a tube and a connector designed to be attached to an end of the tube, characterized in that the connector comprises an appendage designed to be inserted into the tube, the dimensions of the appendage being adapted to the dimensions of the tube in such a way as to exert a set of forces tending to dilate the tube, and a skirt surrounding the appendage in order to define a groove for receiving the tube between the appendage and the skirt, the dimensions of the skirt being provided in such a way as to exert a set of forces tending to compress the tube.

13 Claims, 1 Drawing Sheet

(56) References Cited

U.S. PATENT DOCUMENTS

Figure 1:
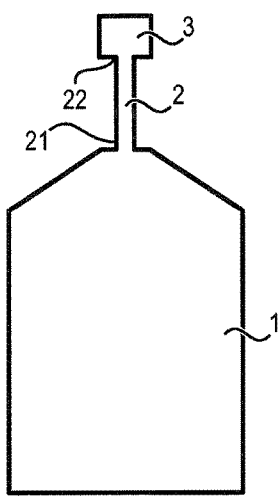

| | | | | |
|---|---|---|---|---|
| 5,312,377 A | * | 5/1994 | Dalton | A61M 39/10 |
| | | | | 285/331 |
| 6,056,724 A | | 5/2000 | Lacroix | |
| 6,129,712 A | | 10/2000 | Sudo et al. | |
| 2004/0116891 A1 | * | 6/2004 | Curutcharry | A61M 39/10 |
| | | | | 604/403 |
| 2006/0217679 A1 | * | 9/2006 | Hanly | A61J 1/10 |
| | | | | 604/403 |
| 2013/0030382 A1 | | 1/2013 | Sudo | |

FOREIGN PATENT DOCUMENTS

| | | | | |
|---|---|---|---|---|
| EP | 0852152 A1 | | 7/1998 | |
| EP | 0998952 A1 | | 5/2000 | |
| EP | 2550985 A2 | | 1/2013 | |
| FR | 2475903 A1 | | 8/1981 | |
| GB | 2067075 A | * | 7/1981 | A61M 39/045 |
| GB | 2067075 A | | 7/1981 | |

OTHER PUBLICATIONS

International Search Report and Written Opinion of the International Searching Authority (Forms PCT/ISA/210, PCT/ISA/220 and PCT/ISA/237) for International Application No. PCT/EP2013/075615, dated Feb. 14, 2014.

\* cited by examiner

ASSEMBLY FOR MEDICAL USE FOR ADMINISTERING A PRODUCT TO A PATIENT

TECHNICAL FIELD

The present invention relates to the general technical field of administering product, in particular liquid product, to a patient, for example by a parenteral route, optionally from a flexible bag.

GENERAL PRESENTATION OF THE PRIOR ART

Assemblies for medical use comprising a tube coupled via one of its ends to a male or female Luer connector are well known and are commonly used to connect various medical devices, especially tubes for conveying a liquid product or viscous product, for example a contrast agent, that is to be administered to a person.

Various types of injectors can be used to inject such a liquid product or viscous product, for example:
- an injector of the "syringe driver" type, comprising a housing designed to receive a syringe that contains the product to be administered, or
- an injector of the "bag" type, such as the one described in the document EP 0 852 152, comprising a housing designed to receive a flexible bag that contains the product to be administered.

When the viscosity of the product to be administered is considerable, the pressure generated in the assembly for medical use, composed of the connector and of the tube, may be very high.

This high pressure may cause leaks to occur at the junction between the tube and the connector of the assembly for medical use.

The document FR 2 475 903 describes a connector device for attaching hoses or the like. The device comprises a frustoconical connection piece and a tubular component surrounding the connection piece, the tubular component forming a gripping means that makes it easier to engage a flexible hose on the connection piece.

The document EP 0 028 198 describes a connector device including a male endpiece and a female endpiece designed to cooperate with each other. The female endpiece has a skirt designed to cooperate either with a skirt of a stopper or with a skirt of the male endpiece.

An object of the present invention is to make available an assembly for medical use which is able to overcome the abovementioned disadvantage. More precisely, an object of the present invention is to make available an assembly for medical use which is composed of a tube and of a connector able to withstand pressures in excess of 11-12 bar or even in excess of 15 or 20 bar.

DISCLOSURE OF THE INVENTION

With this in mind, the invention makes available an assembly for medical use for administering a product to a patient, the assembly comprising a tube and a connector designed to be attached to an end of the tube, the connector having a body and an interface zone at one of the ends of the body, the interface zone comprising:
- an appendage designed to be inserted into the tube, the dimensions of the appendage being adapted to the dimensions of the tube, the external diameter of the appendage being greater than the internal diameter of the tube at its end nearest the body, in such a way as to exert a set of forces tending to dilate the tube, and
- a skirt surrounding the appendage in order to define a groove for receiving the tube between the appendage and the skirt, the internal diameter of the skirt being less than or equal to the external diameter of the tube at its end nearest the body, in such a way as to exert a set of forces tending to compress the tube.

Since the dimensions of the appendage and of the skirt of the connector are adapted to the dimensions of the tube, so as to allow stresses to be applied to the latter, it is possible to limit the risk of leaks at the junction between the connector and the tube. Indeed, this allows the interface zone to subject the tube to sets of radial forces in opposite directions tending to crush the tube in its thickness.

The appendage and the skirt are in one piece. The fact that the interface zone is made in one piece makes it possible to improve the leaktightness of the assembly at the junction between the connector and the tube. More precisely, the fact that the appendage and the skirt are integrally connected limits the risks of leaks compared to an interface zone composed of several elements connected to one another by welding or adhesive bonding. Indeed, in the case of an injection at high pressure, leaks may occur, for example, at the connecting zones of the various elements constituting the interface zone if the latter is composed of several components.

The connection between the tube and the connector can be made by force-fit engagement of the tube in the receiving groove defined between the appendage and the skirt of the connector.

Advantageously, the end of the connector opposite the end having the skirt and the appendage can comprise a head for attachment to another connector. The shape of this head may vary. For example, it is adapted to cooperate with the head of another connector. This allows the assembly for medical use according to the invention to be attached to existing systems for conveying product to be administered to a patient.

Alternatively, the end of the connector opposite the end having the skirt and the appendage can comprise another appendage designed to be inserted into another tube, and another skirt surrounding the other appendage, the dimensions of the other appendage being provided to exert a set of forces tending to dilate the other tube, and the dimensions of the other skirt being provided to exert a set of forces tending to compress the other tube.

The connector of the assembly for medical use can also comprise a substantially cylindrical axial channel between its two ends. Alternatively, the channel can be bent depending on the intended use.

A "substantially cylindrical" axial channel is understood to mean an axial channel whose base is oval, round or frustoconical.

In some alternative embodiments, the skirt comprises a frustoconical inner face opposite the appendage, the diameter of the inner face of the skirt increasing in the direction of its free end. This can make it easier to insert the tube into the receiving groove. Alternatively, the inner face of the skirt can comprise at least one bead which extends toward the appendage and of which the dimensions are provided to induce the application of a set of forces to the tube, this set of forces tending to compress the tube once the latter has been attached to the connector.

Similarly, the appendage can comprise a frustoconical outer face opposite the skirt, the diameter of the outer face of the appendage decreasing in the direction of its free end.

This can also make it easier to insert the tube into the groove. Alternatively, the outer face of the appendage can comprise at least one bead which extends toward the skirt and of which the dimensions are provided to induce the application of a set of forces on the tube, this set of forces tending to dilate the tube once it has been attached to the connector.

In addition to the advantages cited above, the combination:
- of a frustoconical inner face of the skirt, of which the diameter increases in the direction of the end of the connector opposite the tube, and
- of a frustoconical outer face of the appendage, of which the diameter decreases in the direction of the end of the connector opposite the tube, makes it easier to remove the connector from the mold during its production.

Indeed, in some embodiments, the connector can be in one piece. More precisely, the connector can be made in a single piece in order to limit the risks of mechanical play between its various constituent parts, for example the risks of mechanical play between the skirt and the appendage if these are made from two separate components. In other embodiments, the connector can be made of several component parts (for example a first component including an appendage and a channel, and a second component composed of the skirt) which are joined to one another to form the connector.

The appendage can comprise a breakable portion extending along a longitudinal axis at its free end designed to be coupled to the tube. This makes it possible to maintain aseptic conditions in the tube before it is used to administer the product to the patient. Preferably, the breakable portion has at least one wing extending outwardly perpendicular to the longitudinal axis of the breakable portion in order to facilitate its separation from the connector. Advantageously, said wing can have the shape of a portion of a sphere. This makes it possible to limit the risks of perforation of the tube when it is being manipulated in order to detach the breakable portion from the rest of the connector.

In some embodiments, the breakable portion can comprise four wings extending outwardly perpendicular to the longitudinal axis of the breakable portion, said wings having the shape of a portion of a sphere. In this case, the wings can be offset by an angle of 90° with respect to one another so as to form a ball. This ball shape of the wings makes it possible in particular to avoid the retention of microbubbles by the breakable portion.

Preferably, the material from which the connector is made is polycarbonate. The advantage of this material is that it is not subject to creep when exposed to a high temperature as occurs at the moment of sterilization. It thus allows the tube to be kept clamped by the connector. A material such as polyethylene, for example, is unable to afford this advantage.

Preferably, the tube is composed of several (at least two) layers of materials. Still more preferably, the material from which the inner (internal) part of the tube is made is a layer of ethylene-vinyl acetate (or EVA). This layer of EVA has the property of melting when it is exposed to a high temperature as occurs at the moment of sterilization. This makes it possible to increase the adherence between the connector and the tube once these have been attached, especially during the sterilization of the tube and of the connector after their attachment, this sterilization operation inducing the welding of the connector to the tube. This thus avoids the use of an external adhesive that may cause problems of biocompatibility upon contact with pharmaceutical products such as contrast agents.

The material from which the skirt is made can be transparent or translucent. This makes it possible to visually check that the tube is inserted as far as the bottom of the receiving groove during the coupling of the connector to the tube. The outer face of the skirt can also comprise ribs to make it easier to manipulate, especially during the operation of attaching the connector to the tube.

Finally, the assembly for medical use can also comprise a flexible bag containing the product to be administered, this bag being connected to the other end of the tube.

The invention also relates to a connector for medical use designed to be attached to a tube, the connector comprising:
- an appendage designed to be inserted into the tube, the dimensions of the appendage being adapted to exert a set of forces tending to dilate the tube, and
- a skirt surrounding the appendage in such a way that the skirt and the appendage define a groove for receiving the tube, the dimensions of the skirt being adapted to exert a set of forces tending to compress the tube.

The invention also relates to the use of a connector for medical use for connecting a tube for conveying a product to be administered to a patient, the connector comprising:
- an appendage designed to be inserted into the tube, the dimensions of the appendage being adapted to exert a set of forces tending to dilate the tube, and
- a skirt surrounding the appendage in such a way that the skirt and the appendage define a groove for receiving the tube, the dimensions of the skirt being adapted to exert a set of forces tending to compress the tube.

PRESENTATION OF THE FIGURES

Figure 2:
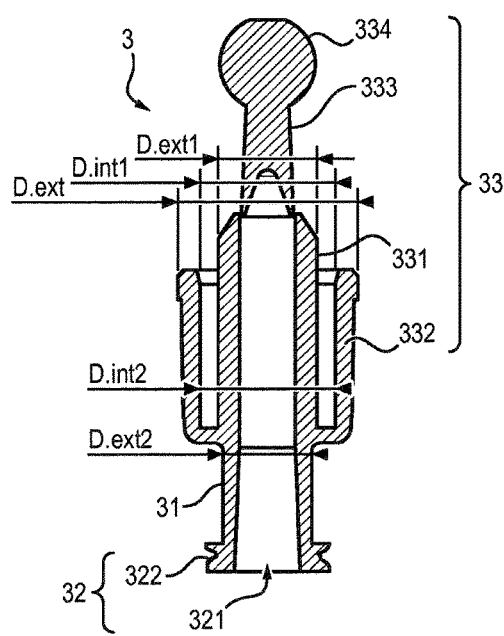
Figure 3:
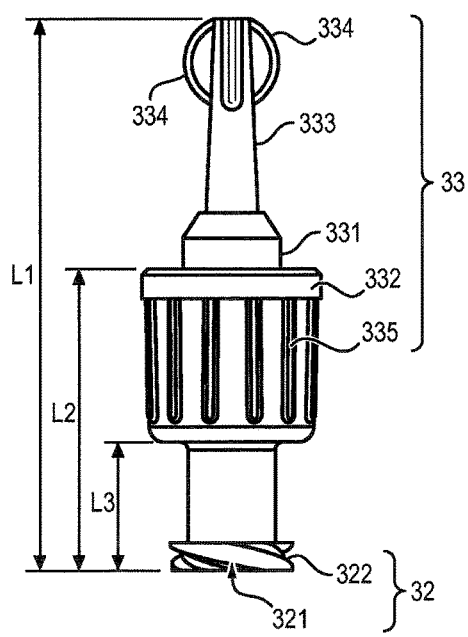

Other features and advantages of the invention will become clear from the following description which is purely illustrative and non-limiting and which must be read with reference to the accompanying drawings, in which:

FIG. 1 shows an example of an assembly for medical use according to the invention, FIGS. 2 and 3 are a perspective view and a sectional view, respectively, showing an example of a connector of the assembly for medical use.

DESCRIPTION OF EMBODIMENTS OF THE INVENTION

The invention will now be described in more detail with reference to the figures. In these figures, elements that are equivalent are designated by the same reference numbers.

Assembly for Medical Use

Referring to FIG. 1, this shows an example of an assembly for medical use comprising a bag 1, a tube 2 and a connector 3.

The medical bag 1 has two superposed leaves of suitable length and width which are composed of several stratified thin film layers made of flexible or pliable materials, optionally transparent or translucent, for example the polymer materials comprising polyethylene and polypropylene, and preferably thermoplastic materials.

The proximal end 21 of the tube 2 is connected to the upper part of the bag 1. This tube 2 is sealed between the superposed films. The distal end 22 of the tube 2 is attached to the connector 3 for coupling the bag 1 to a fluid transfer kit connected to the patient.

Connector

The connector 3 is shown in FIGS. 2 and 3.

It comprises a substantially cylindrical body 31, a locking zone 32 at one of the ends of the body 31, and a tube interface zone 33 at the other end of the body 31.

An axial passage is formed in the body 31 and the zones 32, 33 such that the liquid to be administered is able to flow through the connector 3.

The connector 3 is preferably made of polycarbonate. The inner (or internal) part of the tube is preferably a layer of ethylene-vinyl acetate (or EVA). The use of such materials makes it possible to increase the adherence between the connector 3 and the tube 2 after their sterilization, once they have been joined together to form the assembly for medical use.

Locking Zone

The locking zone 32 of the connector 3 has a head for coupling the assembly for medical use to a transfer kit connected to the patient.

This head includes, for example, an endpiece 321 designed to engage in a head of another connector and/or a collar (not shown) designed to retain the head of another connector.

The endpiece 321 and/or the collar can comprise radially extending teeth 322 or a thread for snap-fitting them or screwing them onto the head of the other connector.

A cap can be provided in order to cover the head of the connector before the latter is coupled to another connector. In this way, it is possible to avoid the risks of bacterial contamination of the assembly for medical use.

The material from which the cap is made is preferably chosen in such a way as to limit the adherence between the cap and the head, even after their sterilization.

Interface Zone

The interface zone is composed of:
an appendage 331 designed to be inserted into the end of the tube 2 of the assembly for medical use, and
a skirt 332 which surrounds the appendage 331 and into which the end of the tube is designed to be inserted.

Appendage

The appendage 331 is of frustoconical shape so as to permit its engagement by friction in the tube 2. The external diameter of the appendage 331 is adapted to the internal diameter of the tube 2.

More precisely:
at its end farthest from the body, the external diameter of the appendage 331 is slightly smaller than or equal to the internal diameter of the tube 2, which makes it easier to insert the appendage 331 into the tube 2,
at its end nearest the body, the external diameter of the appendage 331 is slightly greater than the internal diameter of the tube 2; thus, when the appendage 331 is engaged in the tube 2, it subjects the tube 2 to a set of forces tending to dilate the tube 2.

The connector 3 can comprise a breakable portion 333 at the end of the appendage 331 opposite the body 31 of the connector 3. The breakable portion 333 comprises at least one wing 334 shaped as a portion of a sphere and extending radially outward.

The breakable portion 333 preferably comprises four wings 334:
extending radially outward,
shaped as a portion of a sphere, and
offset by 90° with respect to one another in order to form a ball.

This ball shape of the wings 334 makes it possible to avoid the risks of injury to a user when the assembly for medical use is being manipulated in order to separate the breakable portion from the connector. Moreover, the ball shape makes it possible to avoid the retention of microbubbles. Finally, the ball shape makes it possible to avoid the risk of perforation of the tube 2 when the assembly for medical use is being manipulated in order to separate the breakable portion 333 from the connector 3.

Skirt

The skirt 332 extends at the periphery of the appendage 331 in such a way as to surround the latter, the inner face of the skirt 332 facing the outer face of the appendage 331.

The dimensions of the skirt 332 are adapted to avoid any spreading, in particular inflation, of the tube 2 in the event of an increase of the pressure inside the latter.

The skirt 332 is of frustoconical shape in order to allow the tube 2 to be engaged by friction in the skirt 332. The internal diameter of the skirt 332 is adapted to the external diameter of the tube 2.

More precisely:
at its end farthest from the body, and over a very short distance, that is to say less than 10% of the depth of the groove, the internal diameter of the skirt 332 is greater than or equal to the external diameter of the tube 2;
at its end nearest the body, the internal diameter of the skirt 332 is slightly less than the external diameter of the tube 2.

Thus, when the tube 2 is engaged in the skirt 332, the skirt 332 subjects the tube 2 to a set of forces tending to compress the tube 2.

The outer face of the skirt 332 can comprise ribs 335 extending radially outward in order to make it easier to grip, especially when screwing/unscrewing a cap mounted on the tube interface zone prior to its being joined to the tube in order to form the assembly for medical use.

The skirt 332 is preferably transparent or translucent so as to make it possible to visually check the quality of the attachment between the connector 3 and the tube 2. In particular, the fact that the skirt 332 is transparent or translucent makes it possible to check that the tube 2 is correctly inserted as far as the bottom of the volume defined by the appendage 331 and the skirt 332.

Combination of Appendage and Skirt

It will thus be appreciated that the appendage 331 and the skirt 332 form a groove for receiving the tube 2.

This groove preferably has a V-shaped cross section such that, once inserted into the receiving groove, the tube interface zone subjects the tube 2 to sets of radial forces in opposite directions tending to crush the tube 2 in its thickness, so as to avoid any risk of the product to be administered leaking at the interface between the tube 2 and the connector 3.

The table below gives examples of values:
for the external diameter (D.ext) of the skirt 332, and the internal diameter of the skirt 332 at its end farthest (D.int1) from the body 31 and at its end nearest (D.int2) to the body 31,
for the external diameter of the appendage 331 at its end farthest (d.ext1) from the body 31 and at its end nearest (d.ext2) to the body 31,
the total length L1 of the connector 3,
the length L2-L3 of the tube interface zone of the connector 3, and
the length L3 of the locking zone of the connector 3.

| Dimensions | Ranges of values (in mm) |
| --- | --- |
| D.ext | 10 to 12, preferably 10.5 to 10.7 (still more preferably 10.6) |
| d.ext1 | 6.35 to 6.45 (preferably 6.40) |
| d.ext2 | 6.45 to 6.55 (preferably 6.50) |
| D.int1 | 8.75 to 8.85 (preferably 8.80) |
| D.int2 | 8.69 to 8.79 (preferably 8.74) |
| L1 | 30 to 40 (preferably 36.5) |
| L2 | 15 to 25 (preferably 20) |
| L3 | 7 to 10 (preferably 8.5) |
| L2-L3 | Greater than 9 mm (preferably ≥10) |

These dimensions allow a person skilled in the art to produce an example of a connector that can be used to solve the technical problem addressed by the invention.

The length L2-L3 defines the zone of adhesion between the tube and the connector. The difference between the diameters D.ext and D.int of the skirt makes it possible to define an example of the skirt thickness sufficient to avoid the inflation of the tube in the event of an increase in the pressure inside the tube. The relations between the other dimensions defined in the table above permit the industrial production of the connector and also the automatic assembling of the assembly for medical use. For example, the dimensions D.int1, D.int2 and d.ext1, d.ext2 make it possible to define frustoconical appendages and skirts. When the connector is produced in a mold, the fact that the skirt and/or the appendage are frustoconical makes it easier to remove the connector from the mold.

Thus, the invention proposes an assembly for medical use which allows a liquid product or viscous product to be administered to a patient without risk of leaking, even when the pressure inside the assembly is considerable.

This assembly can be used to administer different types of product, irrespective of the type of injector used to administer said product.

The reader will appreciate that numerous modifications may be made without departing materially from the novel teaching and the advantages described here.

Therefore, all modifications of this kind are intended to be incorporated within the scope of the accompanying claims.

The invention claimed is:

1. An assembly for medical use for administering a product to a patient, the assembly comprising a tube and a connector designed to be attached to an end of the tube, the tube having an internal diameter and an external diameter, the connector having a body and an interface zone designed to be attached to an end of the tube at one of the ends of the body, wherein the interface zone comprises:
   an appendage having an external diameter and designed to be inserted into the tube, dimensions of the appendage being adapted to dimensions of the tube, the external diameter of the appendage-being greater than the internal diameter of the tube at its end nearest the body, in such a way as to exert a set of forces tending to dilate the tube, and
   a skirt having an internal diameter and surrounding the appendage in order to define a groove for receiving the tube between the appendage and the skirt, the skirt having an inner face opposite the appendage, said inner face frustoconical, the internal diameter of the skirt being less than the external diameter of the tube at an end of the skirt nearest the body, in such a way as to exert a set of forces tending to compress the tube, and the internal diameter of the skirt increasing from the end of the skirt nearest the body in a direction of a free end of the skirt.

2. The assembly as claimed in claim 1, wherein the connector additionally comprises a head for attaching said connector to another connector, and a substantially cylindrical axial channel between the appendage and the head.

3. The assembly as claimed in claim 1, wherein the appendage comprises a frustoconical outer face opposite the skirt, the diameter of the outer face of the appendage decreasing in the direction of its free end.

4. The assembly as claimed in claim 1, wherein the connector is molded in one piece.

5. The assembly as claimed in claim 1, wherein the appendage comprises a breakable portion extending along a longitudinal axis at the free end of the appendage, said breakable portion having at least one wing extending outwardly perpendicular to the longitudinal axis, said wing having the shape of a portion of a sphere.

6. The assembly as claimed in claim 5, wherein the breakable portion comprises four wings extending outwardly perpendicular to the longitudinal axis of the breakable portion, said wings having the shape of a portion of a sphere.

7. The assembly as claimed in claim 1, wherein the connector is made of polycarbonate.

8. The assembly as claimed in claim 1, wherein the skirt is made of a transparent or translucent material.

9. The assembly as claimed in claim 1, wherein the skirt-additionally comprises ribs on its outer face.

10. The assembly as claimed in claim 1, wherein the outer face of the appendage comprises at least one bead extending toward the outside.

11. The assembly as claimed in claim 1, wherein the connector additionally comprises another appendage designed to be inserted into another tube, and another skirt surrounding the other appendage, the dimensions of the other appendage being provided to exert a set of forces tending to dilate the other tube, and the dimensions of the other skirt being provided to exert a set of forces tending to compress the other tube.

12. The assembly as claimed in claim 1, which assembly additionally comprises a flexible bag containing the product to be administered, said bag being connected to another end of the tube.

13. The assembly as claimed in claim 1, wherein the groove has a V-shaped cross section such that, once inserted into the groove, the interface zone subjects the tube to sets of radial forces in opposite directions tending to crush the tube in thickness.

* * * * *